United States Patent [19]

Kushner et al.

[11] 4,151,749
[45] May 1, 1979

[54] LIQUID SAMPLING APPARATUS

[75] Inventors: Jack Kushner, Lindenhurst; Henry G. Zwirblis, Nesconset, both of N.Y.

[73] Assignee: Envirotech Corporation, Menlo Park, Calif.

[21] Appl. No.: 821,403

[22] Filed: Aug. 3, 1977

Related U.S. Application Data

[63] Continuation-in-part of Ser. No. 635,981, Nov. 28, 1975, Pat. No. 4,052,904, which is a continuation-in-part of Ser. No. 501,875, Aug. 30, 1974, Pat. No. 3,999,945.

[51] Int. Cl.² .............................................. G01N 1/20
[52] U.S. Cl. .............................. 73/421 R; 73/61.1 R
[58] Field of Search ................ 73/421 R, 421 B, 424, 73/61.1 R; 340/236; 210/DIG. 25

[56] References Cited

U.S. PATENT DOCUMENTS

| | | | |
|---|---|---|---|
| 3,595,089 | 7/1971 | Jirik | 73/424 |
| 3,800,219 | 3/1974 | Fosberg | 340/236 X |
| 3,905,902 | 9/1975 | Hoegberg et al. | 210/DIG. 25 X |
| 3,916,674 | 11/1975 | Miller et al. | 73/61.1 R |
| 3,999,945 | 12/1976 | Kushner et al. | 73/421 R X |

FOREIGN PATENT DOCUMENTS 1399477  4/1965  France ...................... 340/236

*Primary Examiner*—Richard C. Queisser
*Assistant Examiner*—Joseph W. Roskos
*Attorney, Agent, or Firm*—Michael J. Pollock; Robert E. Krebs

[57] ABSTRACT

Disclosed is an apparatus for obtaining a continuous substantially particle-free sample of a liquid comprising a rotatable disc disposed beneath a conduit from which a stream of liquid to be sampled is discharged onto a portion of the disc and a drive motor for rotating the disc at a speed sufficient to form a bed of liquid about the disc periphery. A continuous sample of the liquid is removed by a blade positioned to engage the bead adjacent an edge portion of the disc at a point along the disc periphery opposite the portion wetted by the stream so that any solid particles which may be present in the liquid are carried off in the stream flowing from the disc before reaching the blade.

8 Claims, 2 Drawing Figures

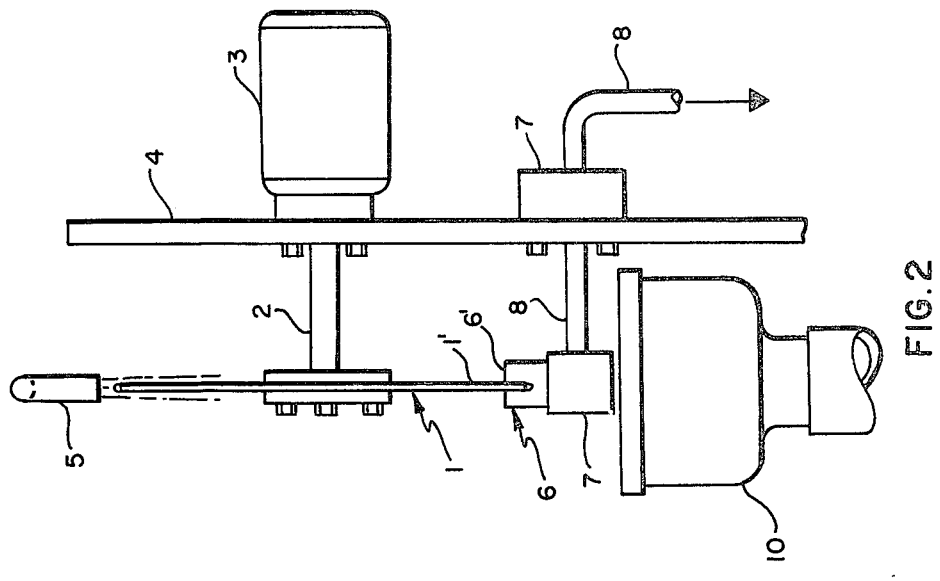
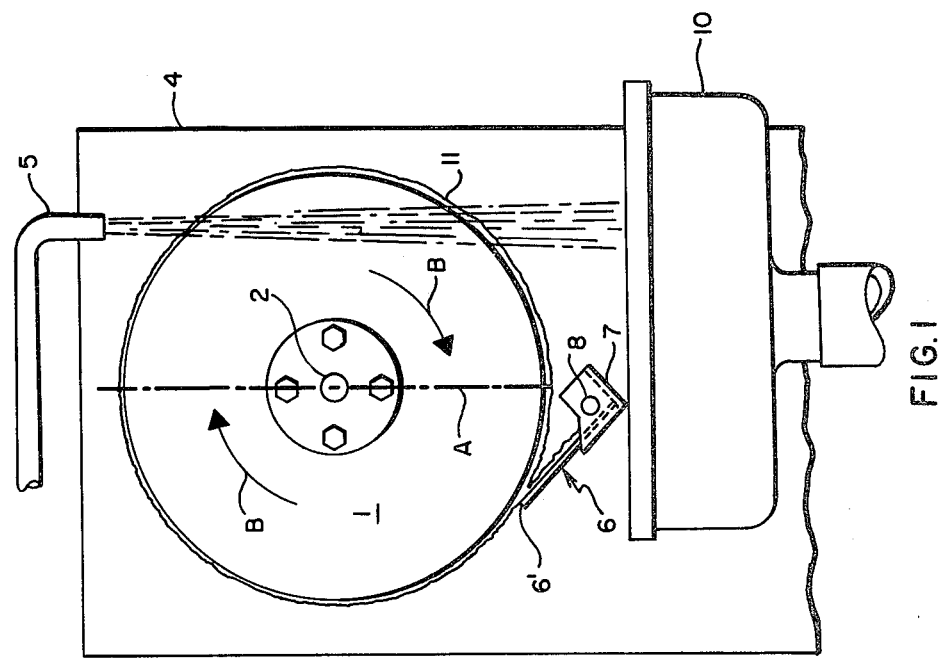

LIQUID SAMPLING APPARATUS

CROSS-REFERENCES TO RELATED APPLICATIONS

This application is a continuation-in-part of our co-pending U.S. application, Ser. No. 653,981, filed Nov. 28, 1975, now U.S. Pat. No. 4,052,904 entitled "Apparatus For Obtaining A Relatively Particle-Free Sample Of A Liquid". Application Ser. No. 635,981 is in turn a continuation-in-part of our U.S. patent application, Ser. No. 501,875, filed Aug. 30, 1974, entitled "Liquid Analysis System", now U.S. Pat. No. 3,999,945.

BACKGROUND OF THE INVENTION

The invention relates to an apparatus for collecting a continuous sample of a liquid for subsequent chemical analysis or other tests. While the sampling apparatus of the invention may be employed in any liquid analysis system, it is particularly suited for use with automated analysis equipment in municipal water supply and waste water monitoring systems, commercial process control systems, industrial fluid waste surveillance systems, and the like.

With increasing public concern over the quality of the environment, a significant need has arisen for equipment which is capable of accurately and economically testing various environmental conditions. Conventionally, if one wishes to measure the level of pollutant, the biological oxygen demand or some other parameter of a body of water, one would take a sample of the water and submit it to an appropriate quantitative chemical analysis. These chemical tests generally comprise a number of steps involving the mixing and reacting of a predetermined amount of the sample or reacted sample with specific quantities of various chemical agents.

These tests are best carried out individually by relatively highly skilled personnel. Naturally, if one wishes to use a test to obtain data continuously or at frequent intervals and thus construct an accurate and complete picture of the state of water quality over a period of time, conventional manual testing is quite expensive. If, on the other hand, the continuous analysis is to be performed with automated equipment, it is necessary to have a technique for taking a continuous sample from the body of water or other liquid to be tested.

For the proper operation of such systems employing automated test equipment, the sample must be representative of the liquid to be tested and chemically unaltered in order for the results of the subsequent analysis to give a true indication of its quality. Simply diverting a portion of the liquid from the body, however, will not provide acceptable results because the thus obtained sample tends to include solid particles which interfere with the proper operation of automatic analysis equipment. This problem is particularly accute in automated systems for monitoring of waste water or industrial effluents containing sand, debris such as hair, paper shreds, and other floating and suspended particles which tend to clog the equipment within a relatively short time. The sample collected for testing must, therefore, be not only representative, but in addition, must also be relatively free from foreign matter.

The object of this invention is to provide an economic and reliable apparatus for automatically obtaining from a liquid to be tested a continuous representative sample substantially free from solid particles which is capable of extended operation with minimal maintenance.

SUMMARY OF THE INVENTION

In accordance with the preferred embodiment, the sampling apparatus includes a rotatable disc, means, such as a pipe, for discharging a stream of the liquid to be tested onto a portion of the disc and a drive motor for rotating the disc at a sufficient speed to form a bead of liquid about its periphery under the influence of centrifugal force. As the disc rotates, a collecting blade adjacent the edge of the disc engages the bead and continuously removes a sample of the liquid which then flows into a collecting vessel connected to a conduit leading to a chemical analyzer or other test equipment. The sample collecting blade may preferably be in the form of a flat strip which extends from the disc to the collecting vessel and is inclined from the vertical to facilitate the flow of the liquid removed from the disc by its upper edge.

Advantageously, the disc is rotated in the direction of the flow of liquid discharging from the pipe to reduce turbulence and the collecting blade is positioned to engage the bead at a point along the disc periphery opposite the spot at which the stream impinges on the disc. For example, the pipe may be positioned above the disc and to one side of its vertical center line so that the downwardly flowing stream of liquid impinges on an upper edge portion of the disc. The blade is disposed on the other side of the vertical center line adjacent an opposite, lower portion of the disc. In such an arrangement, as the edge of the disc rotates out of the stream discharging from the pipe, any solid particles which may be present in the liquid are carried off in the stream flowing away from the disc before reaching the blade. The sample collected by the blade is therefore substantially free from foreign matter which would otherwise clog the conduit leading to the test equipment and/or interfere with the proper operation of the sampling apparatus.

To further reduce the possibility that lighter particles with a propensity to adhere to the disc surface, such as hair, paper shreads, grease, and the like, would be picked up and enter the sample collecting system, the blade may be spaced from the surface of the disc a distance sufficient to engage the bead of liquid without direct contact with the disc itself. Even though in such an arrangement the collecting blade removes only a portion of the bead, the apparatus is nevertheless capable of delivering the sample at a high flow rate because of the relatively thick bead that can be formed by rotating the disc at a speed close to that at which the centrifugal force starts to impel the liquid away from the disc periphery.

The sampling apparatus of the invention thus in effect pre-treats the liquid to be tested by filtering out particulate matter and delivers to the test equipment a continuous sample which is substantially free from solid contaminants. The apparatus is, in addition, self-cleaning since any particles which may initially cling to its surface are washed away during subsequent rotations of the disc through the stream of liquid preventing the build-up of sludge or other foreign matter. This mode of operation and the simple construction of the apparatus thus enables the system to operate for long period with very little maintenance.

BRIEF DESCRIPTION OF THE DRAWINGS

FIG. 1 is an elevation view of a liquid sampling apparatus in accordance with the invention; and FIG. 2 is a side view of the sampling apparatus shown in FIG. 1.

DETAILED DESCRIPTION OF THE PREFERRED EMBODIMENT

Referring now to the drawings, the sampling apparatus shown in FIGS. 1 and 2 includes a rotatable disc 1 attached to shaft 2 of a drive motor 3 which is secured to a mounting plate 4. The liquid to be sampled is conducted to the apparatus through a pipe 5 which is positioned above the disc 4 and to one side of its vertical center line A such that the stream of liquid discharges from the end of the pipe onto an upper edge portion of the disc. A sample collecting blade 6 is disposed on the other side of the vertical center line A adjacent a lower portion of the disc at a point along the disc periphery opposite the spot at which the stream of liquid impinges on the disc. The liquid flowing from the disc drains into a sink 10 disposed below the disc 1 and in the path of the stream discharging from the pipe 5.

As indicated by arrows B in FIG. 1, the disc is rotated by the drive motor 3 in the direction of the downward flow of liquid discharging from the pipe 5. As also shown in the figures, the collecting blade 6 is in the form of a flat strip with its upper edge 6' parallel to the axis of the disc and positioned adjacent the rim 1' of the disc 1. The blade extends from the disc in a direction opposite to the direction of rotation with the plane of the blade being generally tangent to a line on the rim 1' opposite the upper edge 6'.

The collecting blade 6 extends downwardly from the disc 1 to a cup-like sample collecting vessel 7 and is attached to one of its walls. The interior of the collecting vessel 7 communicates with a conduit 8 which extends through an aperture in the mounting plate 4 and conducts the liquid sample to the chemical analysis or other test equipment. The collecting vessel and blade assembly is affixed to and is supported by the conduit 8, which is in turn secured to the plate 4 by a mounting block 9.

In operation, a portion of the liquid to be sampled, which may for example be municipal or commercial waste water, is conducted to the apparatus through the pipe 5 and discharged onto the disc 1 wetting its surface. At the same time, the disc is rotated by the drive motor at a sufficient speed to force the liquid to form a bead about the disc periphery under the influence of centrifugal force. As the disc rotates, the upper edge 6' of the collecting blade engages the bead, indicated generally at 11 in FIG. 1, and removes a portion of the liquid from the disc. The liquid sample then flows along the blade into the collecting vessel 7 and from there is conducted to the test apparatus via conduit 8.

Rotating the disc in the direction of the stream discharging from the pipe, as well as positioning the blade so that it extends from the disc in a direction opposite to the direction of rotation, minimizes turbulence in the region of the blade and the region at which the stream impinges on the disc. This insures the formation of a uniform bead about the disc periphery and, hence, a uniform flow rate of the sample. The sample flow rate delivered by the apparatus can be controlled by regulating the rotational speed of the disc since the thickness of the bead, and hence the volume of liquid removed by the blade are dependent on the centrifugal force, which in turn is dependent on the rotational speed. Thus, by changing the rotational speed and/or by choosing appropriate dimensions for the disc diameter and thickness, the flow rate of the sample delivered by the apparatus can be adjusted to the requirements of the particular equipment used in a given analysis system.

Moreover, as discussed earlier, due to the relationship of the collecting blade 6 and discharge pipe 5, the sample obtained by the apparatus is substantially free from any solid particles which may be present in the liquid to be tested. Because the blade and discharge pipe are disposed on opposite sides of the disc, the solid particles, which might otherwise cling to the disc surface and be picked up by the blade, are carried off in the stream flowing away from the disc and into the sink. Thus, by the time a given point on the rim of the disc rotates out of the downwardly flowing stream and reaches the collecting blade, the bead presented to the blade is free of particles which would tend to clog the sample collecting and/or analysis systems. As also mentioned earlier and shown in FIG. 1, the upper edge 6' of the blade may be spaced from the rim of the disc a distance such that it engages the bead of liquid without direct contact with the disc itself. With such a construction, should any lighter particles, such as paper shreds, hair, fabric fibers, and the like, cling to the disc surface, they will pass through the gap between the blade and the disc without being picked up by the blade. Any such particles which may cling to the disc, as well as contaminants such as sludge and grease, are then washed from the disc during subsequent passes of the disc through the stream of liquid. The disc is thus continuously cleansed during operation preventing the build-up of sludge on its surface which would otherwise be picked up by the collecting blade and interfere with the proper operation of the apparatus.

To further reduce maintenance requirements, the components of the apparatus exposed to the liquid, such as the disc, blade and collecting vessel, may be made from corrosion resistant material such as fiberglass. Moreover, although in the embodiment shown in the figures and described above, the collecting blade is positioned to engage the bead of liquid on the rim of the disc, the blade may also be positioned to engage the bead on the peripheral side surface of the disc.

We claim:

1. Apparatus for obtaining a continuous, substantially particle-free sample of a liquid comprising:
   (a) a rotatable member having a liquid wettable surface and a generally continuous periphery;
   (b) means for discharging a stream of liquid to be sampled downward onto a portion of said surface;
   (c) means for rotating said member at a speed sufficient to form through the influence of centrifugal force a bead of the liquid to be sampled about the periphery of said member; and
   (d) means for removing a portion of the liquid from said member positioned to engage said bead without direct contact between said removing means and said member.

2. Apparatus according to claim 1 wherein said removing means includes a blade disposed adjacent the periphery of said member in engagement with said bead.

3. Apparatus according to claim 2 wherein said liquid discharging means is arranged to discharge the liquid onto an edge portion of said member and said blade is disposed at a position along the periphery of said member adjacent said edge portion.

4. Apparatus according to claim 3 wherein said member is rotated in the direction of the flow of the liquid in said stream.

5. Apparatus according to claim 4 wherein said discharging means includes a pipe for conducting the liquid to said apparatus, said pipe having an open end disposed above said edge portion so that the liquid is discharged downwardly therefrom onto said edge portion.

6. Apparatus according to claim 5 wherein said blade is positioned to engage said bead of liquid formed on said rim.

7. Apparatus according to claim 6 wherein said blade is in the form of a downwardly extending strip with the upper edge thereof in engagement with said bead, said apparatus further including means disposed adjacent the lower end of said strip for receiving said liquid removed from said disc.

8. Apparatus according to claim 7 wherein said disc is rotated in the direction of the flow of the liquid in said stream and said strip extends from said disc in a direction generally opposite to the direction of rotation of said disc.

* * * * *